United States Patent [19]
Skotnikov et al.

[11] Patent Number: 5,526,705
[45] Date of Patent: Jun. 18, 1996

[54] AUTOMATED WORK STATION FOR ANALYZING SOIL SAMPLES

[75] Inventors: Andrey V. Skotnikov; Vladimier A. Bobrov, both of Minsk, Belarus

[73] Assignee: Tyler Limited Partnership, Benson, Minn.

[21] Appl. No.: 286,768

[22] Filed: Aug. 5, 1994

[51] Int. Cl.⁶ .......................... G01N 33/24; G01N 35/02; G01N 35/10
[52] U.S. Cl. .......................... 73/863; 73/866; 73/863.21; 73/863.23; 422/68.1; 422/82.03; 422/82.09; 422/119; 436/31; 436/145; 436/177
[58] Field of Search .................. 73/863, 863.21, 73/863.23, 866; 204/400; 422/62, 68.1, 82.03, 82.09, 119; 436/31, 145, 177, 178

[56] References Cited

U.S. PATENT DOCUMENTS

| | | | |
|---|---|---|---|
| 2,470,401 | 5/1949 | Horvitz | 436/178 |
| 3,224,512 | 12/1965 | Alexander | 173/19 |
| 3,464,504 | 9/1969 | Stange | 173/28 |
| 3,468,379 | 9/1969 | Rushing et al. | 172/2 |
| 3,986,555 | 4/1975 | Robertson | 166/246 |
| 4,358,054 | 11/1982 | Ehrat | 239/155 |
| 4,587,857 | 5/1986 | Bush | 73/863 |
| 4,588,127 | 5/1986 | Ehrat | 239/156 |
| 4,630,773 | 12/1986 | Ortlip | 239/1 |
| 4,685,339 | 8/1987 | Philipenko | 73/864.45 |
| 4,714,196 | 12/1987 | McEachern et al. | 239/62 |
| 5,033,397 | 7/1991 | Colburn, Jr. | 111/118 |
| 5,050,771 | 9/1991 | Hanson et al. | 222/1 |
| 5,203,212 | 4/1993 | Bovendenr et al. | 73/863.21 |
| 5,220,876 | 6/1993 | Monson et al. | 111/130 |
| 5,266,494 | 11/1993 | Lahoda et al. | 436/177 |

FOREIGN PATENT DOCUMENTS

| | | | |
|---|---|---|---|
| 249972 | 9/1987 | Germany | 436/31 |
| 161851 | 6/1992 | Japan | 73/863 |
| 281883 | 9/1970 | U.S.S.R. | 73/863 |
| 1626240 | 2/1991 | U.S.S.R. | 436/177 |

OTHER PUBLICATIONS

*Using a Multifactor System to Develop Crop Production Recommendations*, by John L. Strauss, Taralon Corporation, Jul. 27–28, 1976, pp. 73–77.

*Blending System Able to Apply Eight Products Simultaneously*, "Outstanding Innovations for 1993" The Agricultural Engineering 50 1993.

*Primary Examiner*—Hezron E. Williams
*Assistant Examiner*—Daniel S. Larkin
*Attorney, Agent, or Firm*—Westman, Champlin & Kelly

[57] ABSTRACT

An apparatus analyzes a plurality of soil samples to determine characteristics of the soil samples. An input portion sequentially provides a plurality of soil samples each having a known solid content. A plurality of vessels are supported for movement with a continuous conveyor relative to the input portion to receive the soil samples. A plurality of testing stations are arranged relative to the continuous conveyor to sequentially access the samples carried by the vessels. The testing stations each test the samples to determine at least one of the characteristics of the samples.

32 Claims, 7 Drawing Sheets

AUTOMATED WORK STATION FOR ANALYZING SOIL SAMPLES

BACKGROUND OF THE INVENTION

The present invention relates to analyzing soil samples. More particularly, the present invention relates to an automated work station for analyzing a plurality of soil samples to determine characteristics of the soil samples.

Generally, all soils may be subdivided into minerals, organic matter, or a mixture of the two, according to the content of the organic material. Depending on the content and size of the particles, the mineral soils are subdivided into varying degrees of four groups: sand, loam, silt and clay. These generally accepted categories are set out on known family particle size class diagrams and soil texture diagrams, both published by the U.S.D.A. and incorporated herein by reference. However, there are also other components such as iron and aluminum hydroxides (sesquioxides), calcium and magnesium carbonates, powder sand (particles having a size of 10–100 micrometers) as well as soil acidity (pH). On the basis of the data obtained with respect to these nutrients and micronutrients, an attempt is made at determining what nutrients must be added to the soil to obtain optimal performance in the field.

The art of site specific crop management, also known as precision farming or site specific agricultural, has grown rapidly in recent years. Conventional site specific crop management involves managing, or treating, soil in a field based on existing or created zonal maps of fields which indicate soil types or other soil characteristics. A problem which has been encountered with existing site specific crop management techniques is the economically efficient collection, correlation and processing or analyzing of soil samples taken from the field. Such processing and analyzing is typically done in order to determine certain attributes, both physical and chemical, of the soil samples obtained. Problems have also been encountered in the manipulation of the attributes, once determined, in order to decide which nutrients to apply to the field, and in actually applying the appropriate nutrients to the field.

In addition, prior analysis techniques took soil samples from a number of locations in a field, and combined the samples to get one overall combined soil sample for a relatively large portion of a field. Typically on the order of 2.5 acres were represented by a single sample. However, it has become known that the chemical and physical attributes of soil can change drastically within, and across, these zones and may overlap between zones. Thus, analyzing on such a spatially infrequent basis leads to inaccuracies.

One of the primary reasons that soil samples were mixed together to obtain a single sample for such a large area, is that analysis of the soil samples has conventionally been extremely time consuming. Soil sample laboratories have conventionally been used in analyzing the soil samples to determine a number of nutrients and micronutrients found in the plants. A portion of the soil sample is taken to different sections of the sampling lab and analyzed for different parameters. Such a process is both time consuming and costly. Therefore, it has been inefficient to separately analyze large numbers of soil samples across a field to obtain a better understanding of the actual physical and chemical properties of the soil across the field.

In addition, another prior system used in attempting to exercise site specific crop management involves the use of USDA soil maps. Such maps are spaciously variable maps which plot what is believed to be the organic matter content of a field on a grid. The USDA soil maps or other data have then been used as the basis for estimating fertilizer requirements at various zones in the field. However, as with the previously methods, it is known that the chemical and physical properties of the soil can, and do, change significantly inside the zones shown on the map.

SUMMARY OF THE INVENTION

The present invention arises from the realization that, if a single sample could be used for sequential testing to determine all of the physical and chemical properties desired, the soil analysis could be speeded up to a point where a much larger number of soil samples could be analyzed in a time and cost efficient manner. The present invention provides a system for analyzing a plurality of soil samples to determine characteristics of the soil samples. An input portion sequentially provides a plurality of soil samples each having a known solid content. A plurality of vessels are supported for movement with a conveyor relative to the input portion to receive the soil samples. A plurality of testing stations are arranged relative to the conveyor to sequentially access the samples carried by the vessels. The testing stations each test the samples to determine at least one of the characteristics of the samples.

DETAILED DESCRIPTION OF THE PREFERRED EMBODIMENTS

Figure 1:
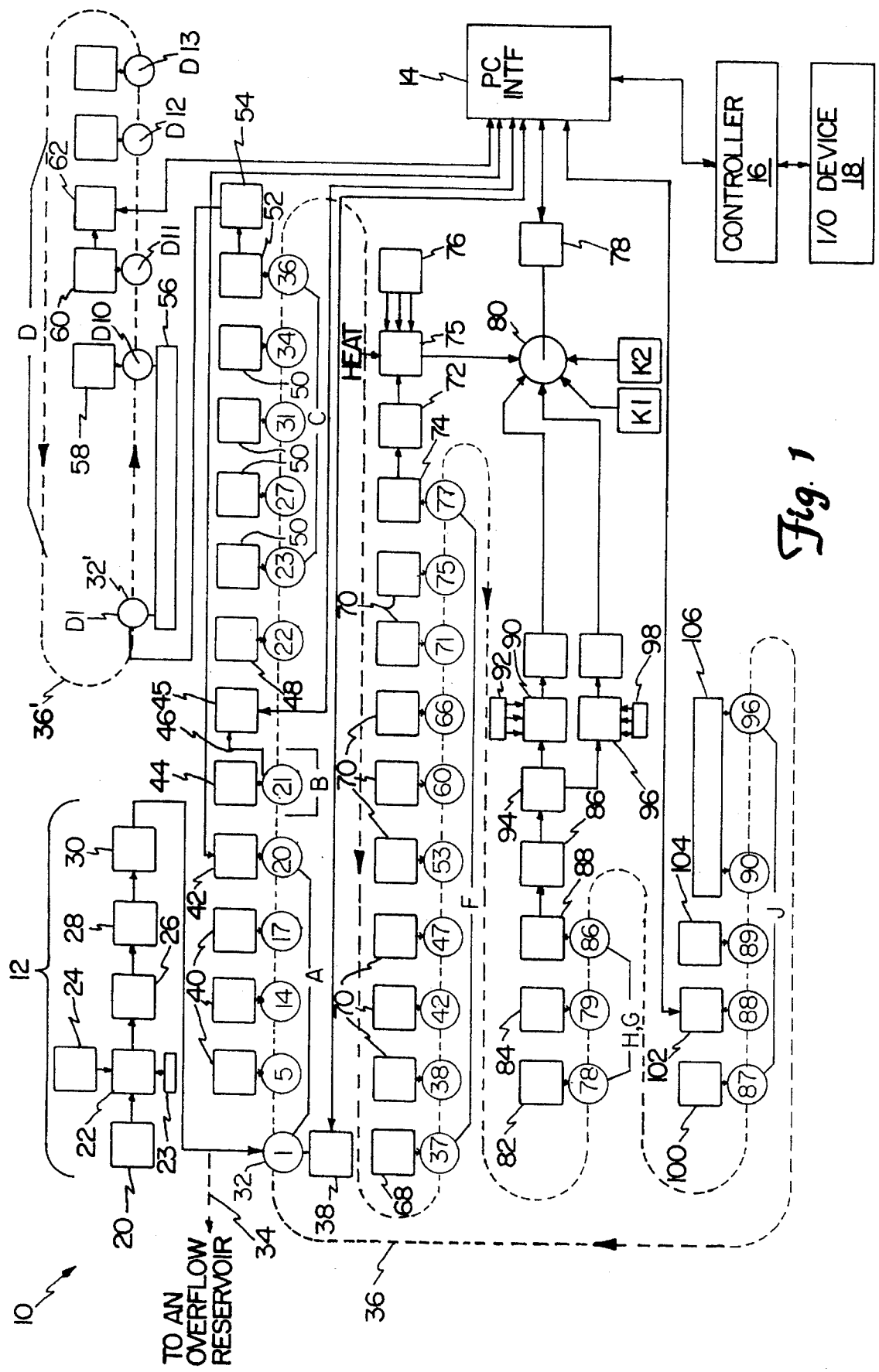
FIG. 1 is a schematic representation of an automated work station according to the present invention.

FIG. 1 is a schematic representation of automated work station 10 according to the present invention. Automated work station 10 includes sample preparation station (or line) 12 and a plurality of test stations, or testing lines A, B, C, D, F, G, H and J. Test station A determines soil acidity, test station B determines soil carbon content, test station C is used to prepare a soil extract which is eventually provided to ion-selective flow sensors for the determination of nutrients and micronutrients in the sample, test station F determines alkali soluble fraction of organic matters, test station G is used to determine organic matter, test station H is used to determine sesquioxides, and test station J is used to determine dust, sand and physical clay in the sample.

Various sensors in the testing lines are coupled to controller interface 14 which is, in turn, coupled to controller 16. Controller 16 is provided with I/O device 18 which is used to communicate with an operator. In the preferred embodiment, controller 16 is preferably a microcontroller, or digital computer. In addition, I/O device 18 preferably includes a monitor or printer, as well as an input device such as a keyboard, a touch screen input device, or a keypad membrane type device. Controller 16 is used to control automated work station 10 and to process the data received from processing lines A–J to provide an output indicative of the nutrients in the soil, and preferably indicative of the type of nutrients to be applied to the field under study in order to obtain optimal performance.

Soil extracts sampled from the field under study are preferably sampled by hydraulic samplers and are automatically packed into plastic bags. The plastic bags are formed from a continuous plastic ribbon, or web, and provided to a sampler bin. The bin is delivered to automated work station 10 and is installed near soil sample preparation line 12.

Soil sample preparation line 12 includes unpacking unit 20, mixing chamber 22, water valve 24, filter 26, humidity meter 28 and volume doser 30. The plastic ribbon containing the soil samples is fed to soil sample unpacking unit 20 which cuts the plastic ribbon containing the soil samples. Each sample content is sequentially fed to mixing chamber 22 which is preliminarily filled with a predetermined quantity of extraction liquid (such as water) through valve 24. The soil sample is agitated homogeneously in mixing chamber 22 by a mechanical stirring mechanism 23. This agitation causes the soil sample and water to be formed into a slurry which is fed through grid filter 26 to a humidity metering unit 28. In the preferred embodiment, grid filter 26 is a filter having 1.0 millimeters standard mesh. Also, in the preferred embodiment, humidity meter 28 is preferably a microwave humidity meter.

The slurry preferably has a volume humidity value from 70% to 80%. A soil slurry sample of approximately 5 milliliters is withdrawn from meter 28 by volume doser 30 and is fed to a first cuvette or vessel 32. In the preferred embodiment, volume doser 30 is a syringe-type doser which is mechanically driven by an electric motor to pull a vacuum in a conduit to remove a given volume of the slurry from humidity meter 28, and provide the extracted volume to vessel 32.

After each dose of the slurry is provided to a corresponding vessel 32, doser 30 preferably draws clean fluid through mixing chamber 22, filter 26, and humidity meter 28 and expels the clear water to an overflow conduit. This is indicated by dashed arrow 34 and serves to clean soil sample preparation unit 12.

Since samples are only dispensed into vessels 32 once per minute, the dose withdrawn from mixing chamber 22 is in humidity meter 28 long enough for controller 16 to take a number of measurements, perhaps as many as 5–10 measurements per dose. These measurements can be averaged to obtain an average humidity reading from humidity meter 28 to increase the accuracy of the results.

In the preferred embodiment, automated work station 10 is provided with a continuous conveyor represented by dashed line 36. Continuous conveyor 36 supports a plurality of vessels 32 for movement with conveyor 36. In the embodiment shown in FIG. 1, vessels 32 are moved through at least 96 different positions with conveyor 36 (83 positions have also been observed to work adequately). At each position, conveyor 36 pauses for a predetermined amount of time, preferably one minute. However, FIG. 1 only shows the positions along conveyor 36 at which the sample contained in the vessels 32 are accessed or manipulated by any external device. The remainder of the positions where no action is taken with respect to the soil samples or slurry samples in the vessels 32 are omitted for the sake clarity. In other words, processing line A shows that, at position 1, the soil sample is weighed by a scale 38. Then, the soil sample is moved through four positions in which no action is taken with respect to the soil sample. Then, at position 5, the soil sample is agitated. Therefore, FIG. 1 only shows positions 1 and 5, which are properly numbered, even though the soil sample actually moves through three additional positions between positions 1 and 5.

After the slurry sample is provided to vessel 32 at position 1 on conveyor 36, the slurry sample is weighed by electronic scale 38. From the measured volume humidity values obtained by humidity meter 28, and from the known weight of the slurry sample in vessel 32, the dry weight (or dry content) of the slurry sample is determined. After a one minute interval, vessel 32 is transferred to the next position in line A.

Line A is used to determine soil acidity and occupies positions 1–20 on conveyor 36. The vessel content is agitated by agitators 40 which are placed relative to conveyor 36 to agitate the contents of vessel 32 at positions 5, 11 and 17. As with the other positions along conveyor 36, the contents of vessel 32 are agitated in positions 5, 11 and 17 for one minute in each position. In position 20, soil pH is measured using a combined pH electrode 42 which is immersed into vessel 32 at position 20. Electrode 42 provides a pH signal indicative of the pH of the slurry in vessel 32 to PC interface 14, which is preferably a parallel interface. Interface 14 provides an output signal, indicative of the pH signal, to controller 16 for use in determining desired micronutrient application levels to the field under study.

Vessel 32 then moves to position 21 which comprises line B—the line for determining soil carbon content. At position 21, vessel 32 is sealed using a cover with a rubber gasket, and concentrated hydrochloric acid (HCl) in a predetermined volume is added to vessel 32 using syringe doser 44. Carbonic acid gas escaping vessel 32 due to the addition of the hydrochloric acid is fed through a conduit 46 in the cover applied to vessel 32 to carbon dioxide volume analyzer 45. Volume analyzer 45 generates an analog signal proportional to the volume of the escaped carbon dioxide gas. The analog volume signal is provided to interface 14 which, in turn, provides a signal indicative of the volume signal to controller 16.

Conveyor 36 then moves vessel 32 to soil extract preparation line C which occupies positions 22–36 on conveyor 36. In position 22, syringe doser 48 is actuated to add distilled water to vessel 32 in an amount required to provide a concentration of extract solution in vessel 32 equal to 1 Molar HCl (1M HCl). The contents of vessel 32 is then agitated at positions 23, 27, 31 and 34 by agitators 50 which are preferably the same as agitators 40. The soil extract in vessel 32 is then filtered and normalized by volume at position 36.

Figure 1A:
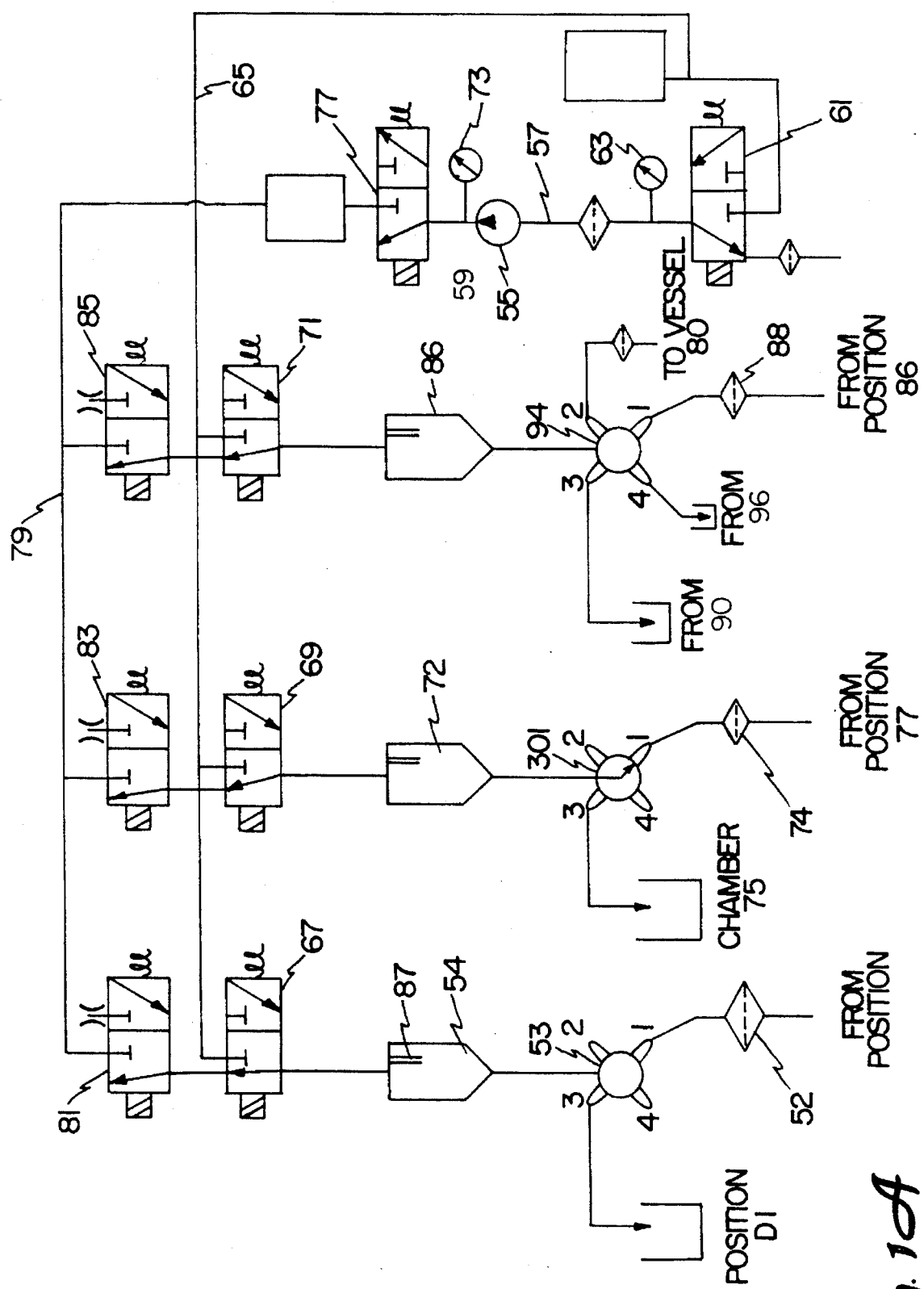
FIG. 1A is a schematic diagram of a portion of the automated work station according to the present invention.

The process of removing the soil extract is shown more specifically in FIG. 1A. An air pump 55 has a vacuum side 57 and a pressure side 59. Vacuum side 57 is coupled through pneumatic valve 61 (and gauge 63) to vacuum line 65. Vacuum line 65 is connected to three pneumatic valves 67, 69 and 71. Pressure side 59 is coupled to a pressure gauge 73 and to pneumatic valve 77. Valve 77, in turn, is coupled via a pressure line 79 to three pneumatic valves 81, 83 and 85. Pump 55 first pulls a vacuum (through actuation of valves 61 and 67) through vacuum line 65. The vacuum withdraws a predetermined volume of filtrate from vessel 32, through filter 52 and cock 53 into vessel-doser 54. Vessel-doser 54 has an electrode (or contacts) 87 which engages the filtrate drawn into vessel-doser 54 at a predetermined level. Upon engaging the filtrate, the electrode provides a signal indicating that the desired filtrate level has been withdrawn from vessel 32 in position 36. In response to this signal, cock 53 is turned and pump 55 (through valve 81) pressurizes vessel 54 to provide the premeasured dose to processing line D preferably through teflon tubing. Any filtrate resting in the feeding tubes to filter 52 is drained back into vessel 32 at position 36.

Referring again to FIG. 1, processing line D includes a second continuous conveyor represented by dashed line 36'. In similar fashion to continuous conveyor 36, conveyor 36' supports a number of vessels 32' for movement through processing line D. Conveyor 36' is preferably driven by the same power source as conveyor 36, and thus vessels 32' remain in each location in processing line D for one minute. While different drive mechanisms could be used to drive conveyor 36 and conveyor 36', the same drive mechanism is preferably used for both conveyors.

The filtrate from doser 54 is provided to vessel 32' at position D1 in processing line D. Processing line D is used to evaporate acid from the soil sample extraction. Thus, a heater 56 is positioned relative to conveyor 36' to provide heat to vessels 32' as they move from position D1 to position D10. The heat causes acids in the dose provided to vessels 32' to evaporate. While ten positions are shown in evaporation line D through which heater 56 provides heat to vessels 32', any suitable number of positions could be used.

Once the filtrate in vessels 32' is evaporated, syringe doser 58 adds into vessel 32' two milliliters of an MES buffer solution having a pH of approximately 6.15. Vessel 32' is then moved to position D11 where peristaltic pump 60 removes a portion of the contents of vessel 32' and provides it, through thin teflon tubing, to ion-selective flow sensor unit 62. A plurality of ion-selective flow sensors are arranged in ion-selective flow sensor unit 62 to determine the concentration of nutrients and nutrients and nutrients and micronutrients such as $K^+$, $Na^+$, $Ca^{++}$, $Mg^{++}$, $NO_3^-$, $NH_4^+$, $H^+$ and phosphate ions. The arrangement of the particular ion-selective sensors is described in greater detail with respect to FIGS. 1B and 1C.

Sensor unit 62 provides a number of outputs to PC interface 14 from the ion-selective flow sensors. These outputs are provided, in turn, to controller 16 which determines and logs the concentration of nutrients and micronutrients in the sensed sample based on the signals from ion-selective flow sensors in unit 62.

Vessels 32' are then washed at position D12 and dried at position D13 for reuse in line D. The evaporation line is preferably covered by a sealed housing having a ventilator, and flexible tubing to extract vapors of hydrochloric acid by an induced draft.

After a filtered dose of the contents of vessel 32 is removed at position 36, vessel 32 enters testing line F which determines alkali-soluble fraction of organic matter, and which occupies positions 37–77 on conveyor 36. Alkali (NaOH) in an amount necessary to produce an ultimate NaOH concentration of 0.1 to 0.2M is added to vessel 32 at position 37 with syringe doser 68. The contents of vessel 32 are then agitated at positions 38, 42, 47, 53, 60, 66, 71 and 75 by agitators 70 (which are preferably the same as agitators 40 and 50). Another extract is removed from vessel 32 by doser 72 at position 77. The extract is filtered through filter 74 and normalized by volume.

FIG. 1A is again illustrative of removal of the extract. Pump 55 first withdraws an extract using valve 69. Doser 72, as with doser 54, has an electrode placed therein for indicating a liquid level to determine the proper liquid volume removed from vessel 32. After withdrawing the predetermined volume of liquid slurry from vessel 32, doser 72 provides the predetermined dose through cock 301 and under pressure provided by pump 55 to mixing cell 75. Chemicals necessary to determine an alkali-soluble organic matter content of the slurry are fed to cell 75 by a three-duct syringe doser 76. Such chemicals and their concentrations and amounts are commonly known.

The concentration of an alkali-soluble fraction of organic matter is determined by an automated photo-electric calorimeter 78. The contents of mixing cell 75 are provided to a flow chamber in calorimeter 78 through a six-duct cock 80. Analog signals from calorimeter 78, which represent a variety of parameters, are provided to PC interface 14. PC interface 14, in turn, provides the signals to controller 16. Cock 80 also has ducts coupled to mixing cells in testing lines F, G and H as described hereinafter.

From position 77, vessel 32 proceeds along conveyor 36 to position 78 where it enters testing line G which determines organic matter in the contents of vessel 32. Testing line G occupies positions 78 to 86 on conveyor 36. At position 78, potassium bichromate dissolved in sulfuric acid is added to vessel 32, in a predetermined amount, using syringe doser 82. Vessel 32 then proceeds to position 79 where heater 84 is immersed in vessel 32 to warm the contents of vessel 32 to a temperature of approximately 90° C. for 50 seconds. Referring again to FIG. 1A, soil extract is removed from vessel 32 at position 86, by syringe doser 86 and is filtered through filter 88. A required dose is fed to mixing vessel 90. Prior to receiving the dose, mixing vessel 90 has chemicals added thereto from 3-duct doser 92. The chemicals added are known chemicals necessary to determine organic matter content using photocalorimetry in calorimeter 78.

Line H is used to determine sesquioxides and begins and ends at position number 86 on conveyor 36. The extract is filtered and normalized by volume by the equipment used in line G. Filtrate is provided through 4-duct cock 94 to mixing cell 96. Prior to receiving the dose, mixing cell 96 has known chemicals added thereto using a 3-duct syringe doser 98, in order to determine sesquioxides. As with the contents of mixing chamber 90, the contents of mixing chamber 96 are provided to calorimeter 78 through cock 80. As shown in FIG. 1A, this can be accomplished using generally the same equipment as used in line G, with only rotating cock 94.

Line J, which occupies positions 87–96 of conveyor 36, is used to determine dust sand and physical clay (particle size). Agitation is provided to the contents of vessel 32 at position 87 by a dedicated stirrer 100 (which is preferably the same as agitators 40, 50 and 70). Stirrer 100 preferably moves up and down, in the vertical direction, within vessel 32 to accomplish agitation. At position 88, vessel 32 is covered by calorimeter/nephelometer 102. Apparatus 102 is used to measure the sedimentation kinetics of dust, sand, and physical clay particles in the upper third of vessel 32 for approximately one minute. Analog signals generated by apparatus 102 are proportional to light transmission, and light scattering, at an angle of 90° and are provided to an analog-to-digital converter in interface 14. Interface 14, in turn, provides digital signals indicative of the analog signals provided by apparatus 102 to controller 16. It should be noted that a number of characteristics of samples can be determined by the calorimeter in one minute. In the preferred embodiment, samples are fed to the calorimeter so that six characteristics or parameters are determined in one minute.

In position 89, vessel 32 is washed by washer 104. Vessel 32 is dried through positions 90–96 by drier 106. After being washed and dried, vessels 32 are again provided to position 1 where they are used to analyze additional soil samples.

Work station 10 can also be expanded. For example, six-duct cock 80 has two unused ducts K1 and K2 which can be used to add additional processing stations to automated work station 10. It should also be noted that, in the preferred embodiment, controller 16 periodically recalibrates all sensors used in work station 10 to maintain accuracy.

Figure 1B:
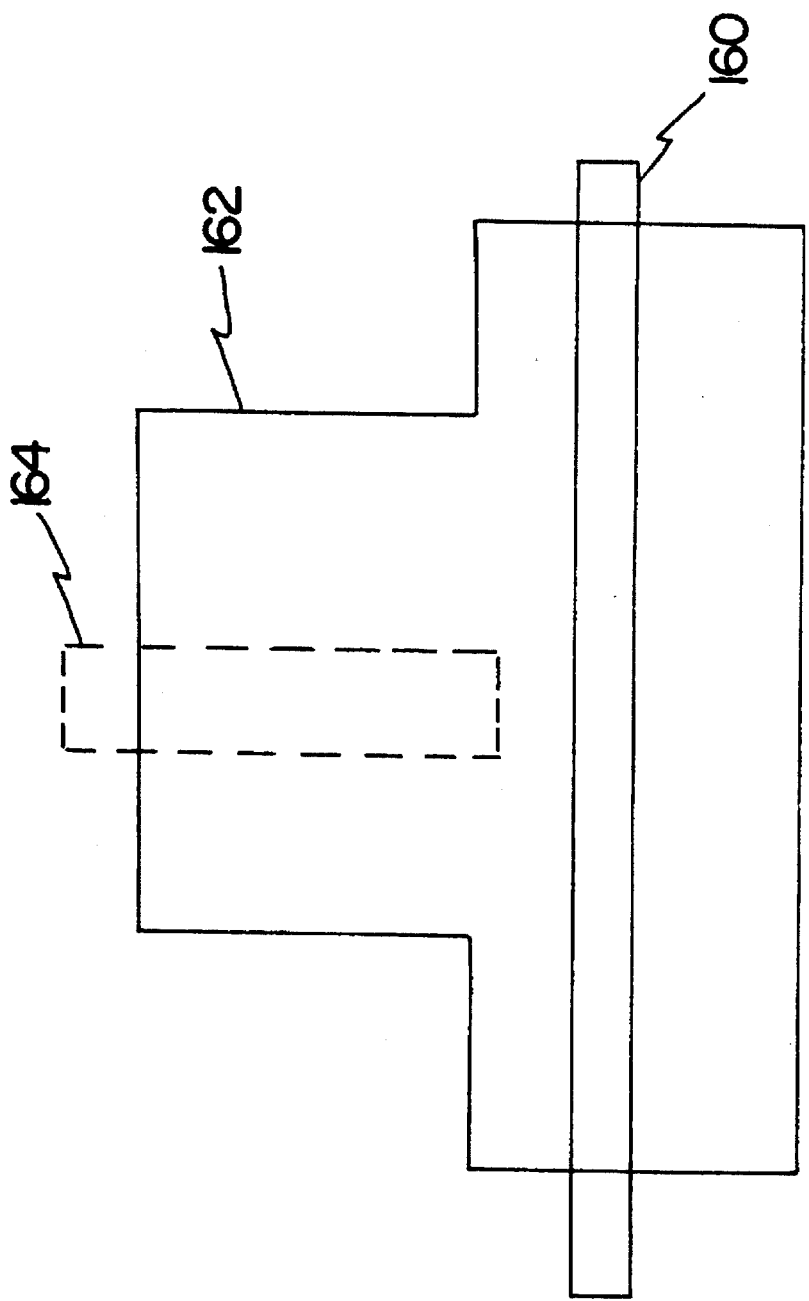
FIG. 1B is a diagram of an ion-selective sensor used with the present invention.
Figure 1C:
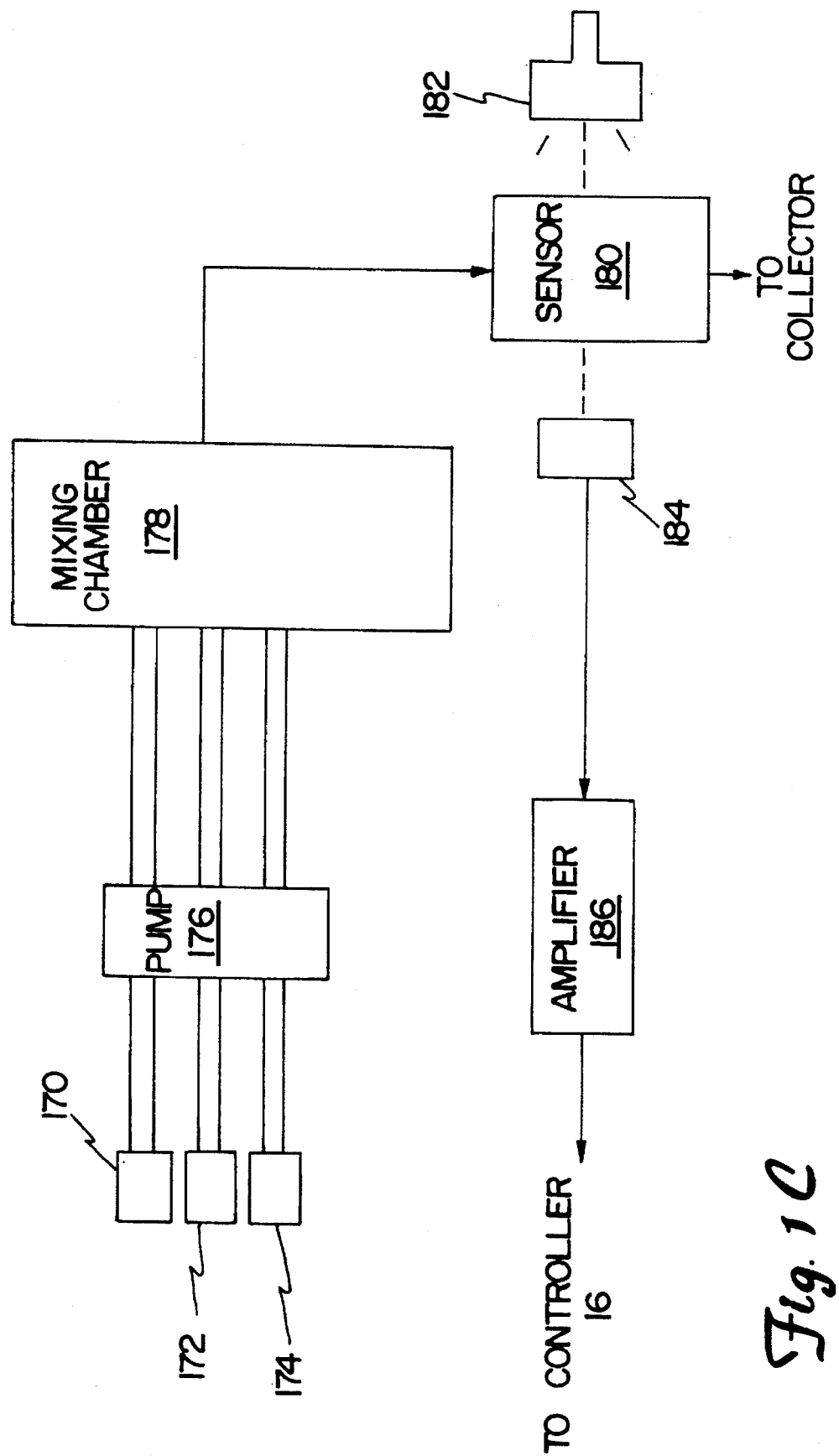
FIG. 1C is a diagram of a phosphate ion concentration sensor used with the present invention.

FIGS. 1B and 1C illustrate the construction of the ion-selective sensors used in ion-selective flow sensor unit 62 to determine the concentration of nutrients in the extraction from the slurry in vessels 32. The sensors include an ion-selective microcapillary sensor 160, a sensor body 162 and an inner reference electrode (preferably a silver/silver chloride wire) 164. A tested solution from a vessel 32 is drawn off by a doser and provided to ion-selective sensors in unit 62. The $H+$ and $Na+$ microcapillary sensors are made of glass ion-selective capillaries having a length of 30 mm and an inner diameter less than 0.5 mm. The $K+$, $NH_4+$, $NO_3-$, $Ca++$ and $Mg++$ microcapillary sensors are constructed on the basis of capillaries made of modified polyvinylchloride and having the same dimensions as the $H+$ and $Na+$ sensors. The sensor body is made of glass. The inner reference electrode is made of silver chloride wire having a diameter of 0.2 mm.

The sensor for measuring phosphate-ion concentration is shown in FIG. 1C. The sensor is a fluxility microcell with a volume of 0.2 ml. It functions based on photocalometric techniques for determining phosphate-ion concentration (the molibdate method) which is well known. A molibdate solution 170, restore solution 172 and measuring solution 174 are provided by pump 176 to a mixing chamber 178. A fluxility measuring sensor 180 is provided between a light source 182 and a photoreceiver 184. A signal amplifier 186 is provided for amplifying the light signal received by photoreceiver 184. The amplified light signal is provided to controller 16 to determine phosphate-ion concentration.

The preferred ion-selective sensors used in the present invention are as follows:

For the potassium ion-sensitive electrode ($K+$):
Response time <30 sec, and the Interval resistance <6 Mohms. The selectivity is based on the following interfering ions and selectivity constants.

| Interfering ion | Selectivity constant |
|---|---|
| $H+$ | $6 \times 10^{-5}$ |
| $Na+$ | $3 \times 10^{-4}$ |
| $Cs+$ | $2.6 \times 10^{-1}$ |
| $NH_4+$ | $1.2 \times 10^{-1}$ |

The service life has been observed to be a minimum of 3 months.

For the sodium sensitive electrode ($Na+$):
Response time <35 sec, and the Interval resistance <50 Mohms. The selectivity is based on the following interfering ions and selectivity constants.

| Interfering ions | Selectivity constants |
|---|---|
| $K+$ | $3 \times 10^{-2}$ |
| $NH_4+$ | $2.0 \times 10^{-2}$ |
| $H+$ | $Ph > Ph^{+3}$ |

The service life is a minimum of 12 months.

For the nitrite ion sensitive electrode ($NO_3-$):
The response time <30 sec, and the Interval resistance <5 Mohms. The selectivity is based on the following interfering ions and selectivity constants.

| Interfering ions | Selectivity constant |
|---|---|
| $Cl-$ | $10^{-3}$ |
| $HPO_4-$ | $10^{-4}$ |
| $SO_4--$ | $10^{-4}$ |
| $H+$ | $Ph > 3$ |

The service life is a minimum of 3 months.

For the ammonium ion sensitive electrode ($NH_4+$):
The response time <40 sec, and the Interval resistance <5 Mohms. The selectivity is based on the following interfering ions and selectivity constants.

| Interfering ion | Selectivity constant |
|---|---|
| $K+$ | $10^{-1}$ |
| $Na+$ | $10^{-4}$ |
| $Ca++$ | $10^{-4}$ |
| $H+$ | $Ph > 3$ |

The service life is a minimum of 3 months. The detection limit is $1.0 \times 10^{-4}$M.

For the calcium sensitive electrode ($Ca++$):
The response time <0.5 minute, and the Interval resistance <5 Mohms. The selectivity is based on the following interfering ions and selectivity constants.

| Interfering ions | Selectivity constants |
|---|---|
| $Mg++$ | $10^{-2}$ |
| $Ca++$ | $10^{-2}$ |
| $H+$ | $pH > 3$ |

The service life is a minimum of 3 months. The detection limit is $1.0 \times 10^{-4}$M.

For the magnesium sensitive electrode ($Mg++$):
The response time <0.5 minute, and the Interval resistance <5 Mohms. The selectivity is based on the following interfering ions and selectivity constants.

| Interfering ions | Selectivity constants |
|---|---|
| $Ca++$ | $5.0 \times 10^{-1}$ |
| $H+$ | $pH > 3$ |

For the hydrogen sensitive electrode ($H+$):
The response time <25 sec., the Interval resistance 20 Mohms, the Test area 1–14 unit of pH, the service life is a minimum of 12 months.

For the phosphate sensitive electrode ($P205-$):
The response time <10 sec., the Interval resistance <20 Mohms, the Test area 10–1000 mkg/ml ($P205$), and the relative error 5–7%.

The reagents preferred are:
1. Solution molibdate: 2.5 g molibdate ammonium $Mo(NH_4)2+50$ ml conc. $HCl+500$ ml distillate $H_2O$.
2. Restore solution: 2.5 g $SnCl_2*2H_2O+100$ ml distillate $H_2O$.

Figure 2:
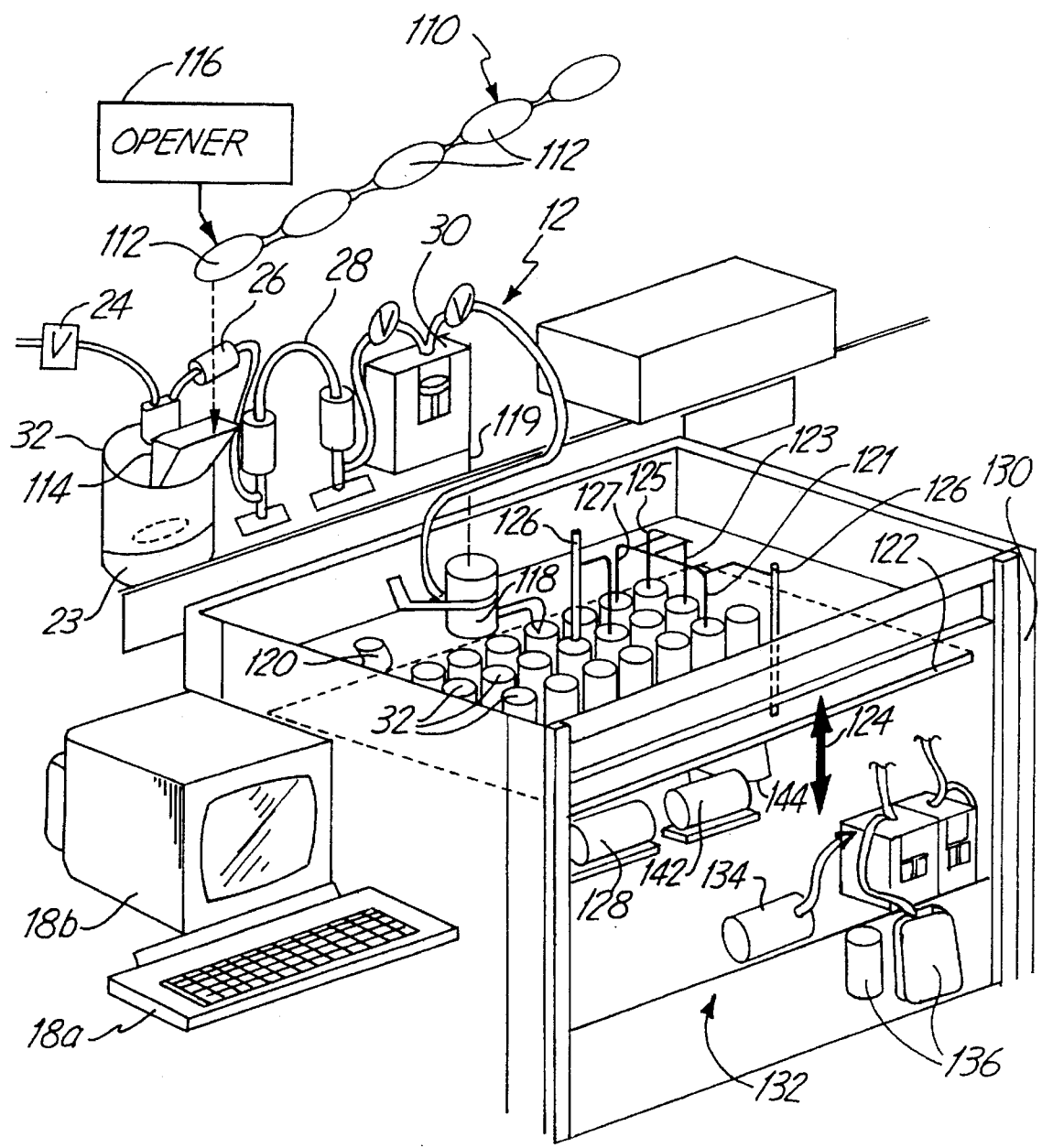
FIG. 2 is a perspective view of one embodiment of the automated work station according to the present invention.

FIG. 2 is a perspective view of a portion of automated work station 10 shown in FIG. 1. Similar items are correspondingly numbered in FIGS. 1 and 2.

FIG. 2 shows sample preparation station 12 and the items comprising station 12. In the preferred embodiment, a web 110 of packages includes a plurality of distinctly sealed package elements 112, each containing a soil sample from a portion of the field under study. However, the package elements 112 are connected to one another and are provided to station 10 by suitable means, such as a continuous conveyor. As package elements 112 approach mixing chamber 22, they are moved adjacent a chute 114 and are opened by apparatus 116. Chute 114 guides the soil from package element 112 into mixing chamber 22. Apparatus 116, is preferably an automated knife or cerrated roller, or another suitable element for opening package elements 112. Water is introduced through valve 24 into mixing chamber 22 and a slurry is formed through agitation by stirrer 23. Stirrer 23 is preferably a mechanical stirrer.

Syringe doser 30 then draws the slurry through filter 26 into humidity meter 28 and provides it to rotatable dispensing nozzle 118 which is mounted for rotation about axis 119. Nozzle 118 provides a known amount of the slurry to one of the vessels 32 which is located over scale 38. After the slurry is dispensed into vessel 32, rotatable nozzle 118 rotates to overflow conduit 120. Doser 30 then draws fresh water through mixing chamber 22, filter 26, and humidity meter 28. This water is discharged through rotatable nozzle 118 into overflow conduit 120 to clean sample preparation station 12. Then, a subsequent packaging element 112 is opened by apparatus 116 and the sample is again introduced into the chute 114 and mixing chamber 22.

As indicated in the description of FIG. 1, automated work station 10 typically has a large number of probes, agitators, doser conduits, and other elements arranged to access vessels 32. A second set of elements can also optionally be arranged to access vessels 32 so that if any of the first set of elements malfunctions, a corresponding one of the second set of elements can be arranged to replace the malfunctioning element. However, for the sake of clarity, FIG. 2 contains only four probes, 121, 123, 125, and 127. Just below vessels 32, work station 10 has a movable platform 122. Platform 122 is movable, such as on linear slides, in the vertical direction indicated by arrow 124. A plurality of standards 126 are rigidly connected to platform 122 for movement therewith. Standards 126 are positioned between vessels 32 so as not to interfere with the movement of vessels 32 and conveyor 36.

Vessels 32 are guided by continuous conveyor 36 (shown in greater detail in FIG. 3) along the route dictated by conveyor 36. Probes which access vessels 32 along conveyor 36 are rigidly connected to standards 126. During movement of vessels 32 with conveyor 36, platform 122 is moved in the upward direction indicated by arrow 124 such that the probes are out of engagement with all of the vessels 32. Conveyor 36 then moves vessels 32 to the next position where appropriate vessels 32 are positioned beneath the probes. Then, platform 122 is controlled to move downward in the direction indicated by arrow 124. This causes the standards 126 to carry the attached probes into vessels 32 which have been moved into position beneath the probes by conveyor 36. Therefore, in order to access the samples in vessels 32, the accessing devices (or probes) are vertically displaced relative to the vessels 32 during movement of conveyor 36, and are vertically introduced into vessels 32 while conveyor 36 is at rest.

Movement of platform 122 is accomplished by electric motor 128. Motor 128 is preferably a stepper motor, or a servo motor, or any other suitable motor controllable by controller 16. In addition, reed switches, or other suitable position sensing switches are placed on frame 130 of work station 10 and on platform 122 to sense movement and position of platform 122 relative to frame 130. The outputs from such position switches are used in controlling motor 128 to raise and lower platform 122.

FIG. 2 also shows that a lower cabinet portion 132 of frame 130 preferably contains the syringe dosers identified in FIG. 1. The syringe dosers are preferably controlled by a vacuum pump or air compressor 134 which supplies air under pressure to work station 10. In the alternative, the syringe dosers can be separately controllable. In addition, FIG. 2 shows that lower portion 132 of frame 130 includes chemical reservoirs 136 for holding a number of chemicals used in the processing and testing lines A–J. The reservoirs 136 are coupled, where appropriate, to syringe dosers for use in work station 10. Further, FIG. 2 shows that I/O device 18 preferably includes keyboard 18a and monitor 18b. Finally, FIG. 2 shows conveyor motor 142 which drives conveyor 36. This is described in greater detail with respect to FIG. 3.

Figure 3:
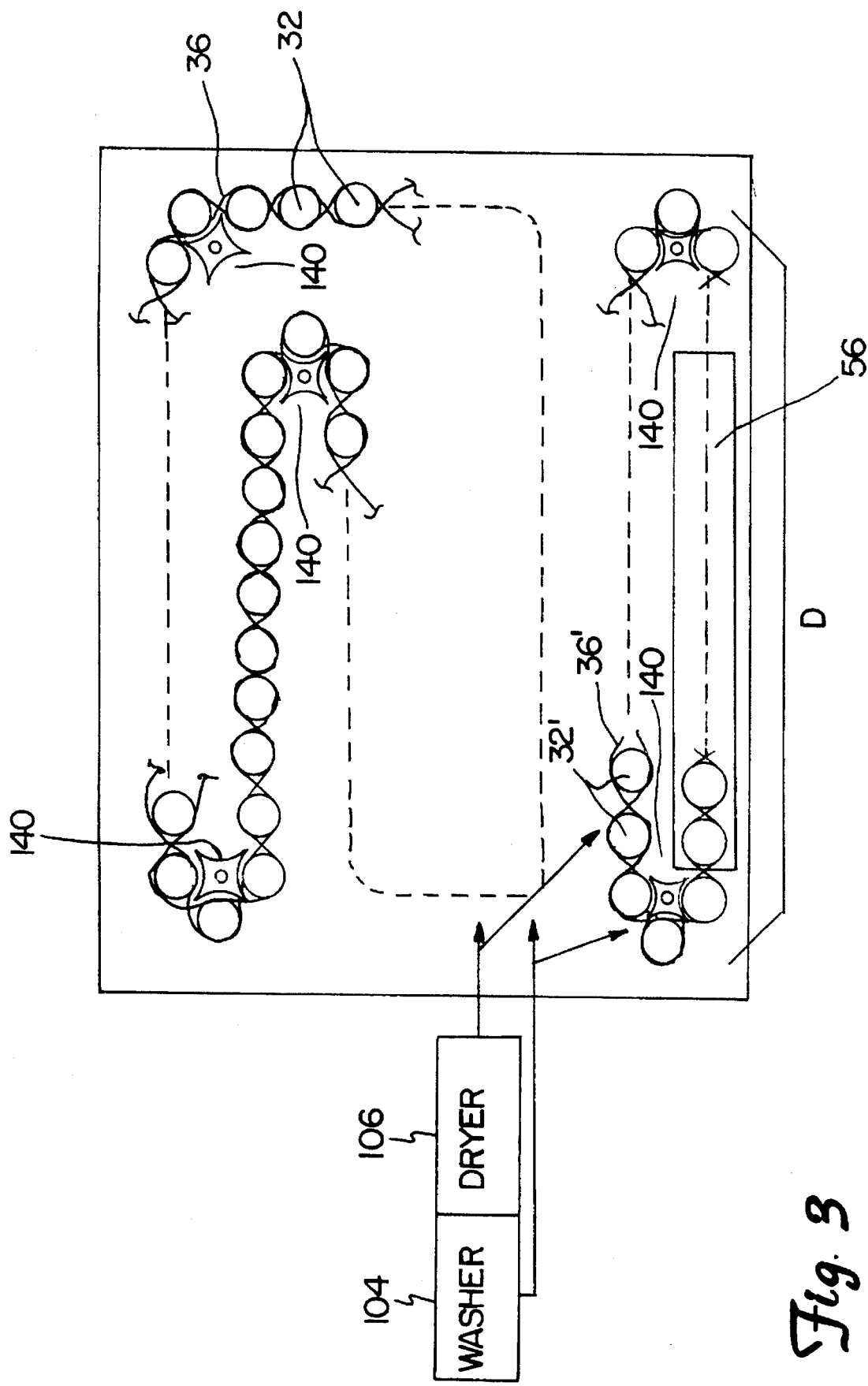
FIG. 3 is a top plan view of a portion of the work station shown in FIG. 2.

FIG. 3 is a top plan view of a portion of work station 10. FIG. 3 illustrates that conveyor 36 is preferably formed of a two-strand plastic link belt, but could also be a disk or other suitable conveyor. The links in the belt are sized to snugly fit about an outer perimeter of vessels 32. Vessels 32 and conveyor 36 are guided by sprockets 140. At least one of the sprockets 140 are driven by conveyor motor 142 (shown in FIG. 2). Conveyor motor 142 has drive shaft 144 and link 146 which mechanically links one of sprockets 140 to motor 142. As with motor 128, motor 142 is preferably a stepper motor, or servo motor, or other suitable motor controllable by controller 16 to advance conveyor 36 at regularly timed intervals.

FIG. 3 also illustrates a portion of testing station D. Testing station D includes conveyor 36' which is similar to conveyor 36 but is preferably a metal link belt. Conveyor 36' is also guided by a plurality of sprockets 140. In the preferred embodiment, conveyor 36' is driven by the same motor 140 as conveyor 36. However, it should be noted that conveyor 36' can also be separately driven.

FIG. 3 shows that heater 56 in test station D comprises a stainless steel heating element over which conveyor 36' moves vessels 32'. In the preferred embodiment, vessels 32' are also formed of stainless steel and are in physical contact with heater 56 as conveyor 36' moves vessels 32' along heater 56. Heat is thus transferred from heater 56 to vessels 32' to evaporate acid from the extracted slurry as previously described with reference to testing station D in FIG. 1.

FIG. 3 further illustrates that washer 104 and dryer 106 can be any suitable washer and dryer, such as a robotic manipulator which injects water into vessels 32, removes vessels 32 from conveyor 36 to dump out the water, replaces vessels 32 in conveyor 36, and heats vessels 32 to dry them. Alternatively, washer 104 and dryer 106 can be fastened to platform 122 and implemented in the form of a cover tightly covering vessel 32. A contaminated vessel is washed out by introducing water, fed through the cover into the vessel 32. The water is then removed either by pumping or by physically manipulating vessel 32 to pour the water out into a waste collector. Vessels 32 are then dried by heated air directed to the interior of vessels 32. Washer 104 and dryer 106 are preferably arranged so they can be commonly used both in test line D, and in test line J. However, separate washers and dryers can be used for the separate lines.

Figure 4:
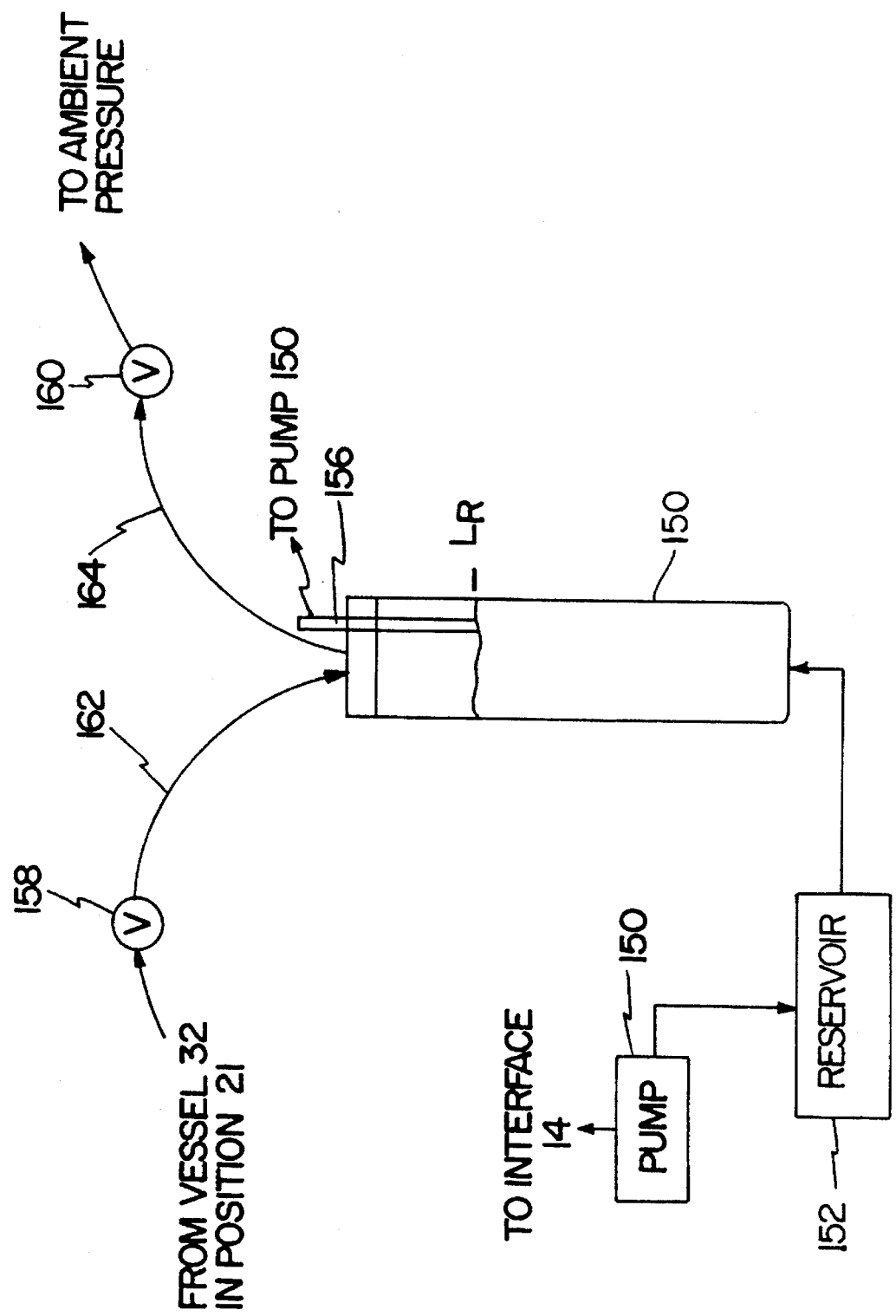
FIG. 4 shows a carbonate volume analyzer used with the present invention.

FIG. 4 illustrates one preferred embodiment of volume sensor 45. Volume sensor 45 includes pump 150, reservoir 152, volume vessel 154 and level sensing electrode 156. In addition, a pair of valves 158 and 160 are coupled to communicate with vessel 154 through conduits 162 and 164. Initially, a calibration liquid is pumped by pump 150 from reservoir 152 into vessel 154 until it reaches a reference level $L_R$. Upon reaching reference level $L_R$, the liquid engages level sensing electrode 156 which provides a signal to pump 150 causing pump 150 to stop pumping liquid into vessel 154. Then, as described with respect to FIG. 1, when hydrochloric acid is added to the slurry at position 21 in line B, carbonic gas is released from the vessel 32 at position 21 and that gas is provided, through valve 158, to vessel 154. The gas gathering in vessel 154 forces the liquid down, away from reference level $L_R$ and back into reservoir 152.

After a desired time interval, pump 150 is again activated and pumps a volume of liquid from reservoir 152 back into vessel 154 to bring the liquid level in vessel 154 back up to the reference level $L_R$. By determining the number of revolutions of pump 150 required to pump the given volume of liquid back into vessel 154, controller 16 can determine the volume of gas which was generated by the slurry in vessel 32 at position 21. This corresponds to the carbonate level in the slurry. After the volume measurement is taken, vent 160 is opened and pressure in vessel 154 is allowed to vent to an ambient pressure.

It has been observed that the automated test station according to the present invention can process approximately 1200 samples in a 20 hour operating period (approximately 60 samples per hour). Time spent to process each sample is approximately 1 minute with a weight of an analyzed sample being preferably 5 grams. Controller 16 is preferably an IBM PC/AT computer with an appropriate serial or parallel interface, preferably a parallel interface containing at least a 10 bit analog-to-digital converter with a 20 channel analog commutator and three 8 bit I/O ports. Controller 16 preferably is coupled, in any suitable manner, to control the conveyor 36 and the motor driving platform 122 in vertical directions, as well as the syringe dosers and other actuators used in sample preparation.

It has also been observed that a preferred time used to move vessels 32 to the next position is approximately 2 seconds. All samples on all the lines are processed synchronously with a 1 minute cycle time.

It should also be noted that the present invention uses ceramic filters in filtering the slurry. Preferred filters are manufactured by Fischer Controls Co. and can be subjected to back pressure for cleaning. This provides significant advantages over paper filters which have been used in past processes.

In conclusion, the present invention provides an automated work station 10 in which soil samples are automatically prepared, processed, and analyzed in sequential order. Since the present invention utilizes only a single soil sample per tested field location and takes all parameters for that location from the single sample, automated work station 10 can provide a throughput of one sample per minute (once the first sample is cycled all the way through cycling lines A–J). This provides significantly increased throughput, and higher efficiency, in analyzing soil samples over prior laboratory analysis methods. Thus, the present invention is suitable for analyzing far greater quantities of soil samples, in far less time, allowing a field under study to be mapped to a very fine grid. This provides significantly higher accuracy in determining the type of soil in the field under study than in prior methods.

In addition, the present invention analyzes soil after preparing it as a slurry. In prior systems, a soil sample is first dried before being analyzed and processed. This drying can result in the loss of certain nutrients and micronutrients (such as nitrogen and potassium) prior to analysis making the analysis results inaccurate. Such inaccuracies, of course, affect the subsequent application nutrients to the field under test.

Also, the present invention uses ion-selective sensors which are placed in the flow of the extraction from the slurry. This allows quicker signal processing based in interferences between the sensors. Placing the sensors in the flow also provides increased speed in obtaining analysis results, and evaporation of HCl. The addition of the MES buffer significantly increases the concentration of ions and the precision of the electrodes.

Although the present invention has been described with reference to preferred embodiments, workers skilled in the art will recognize that changes may be made in form and detail without departing from the spirit and scope of the invention.

What is claimed is:

1. An apparatus for analyzing a plurality of soil samples to determine characteristics of the soil samples, the apparatus comprising:

a sample input section sequentially providing a plurality of soil samples each having a known solid content;

a continuous conveyor;

a plurality of vessels supported for movement with the continuous conveyor relative to the sample input section to receive the soil samples; and a plurality of testing stations arranged relative to the continuous conveyor to sequentially access the samples carried by the vessels, the testing stations each testing the samples to determine at least one of the characteristics of the samples.

2. The apparatus of claim 1 and further comprising:

a controller operably coupled to the testing stations for determining and processing nutrient information based on the characteristics determined by the test stations.

3. The apparatus of claim 2 wherein the controller periodically calibrates the test stations.

4. The apparatus of claim 2 wherein the sample input section comprises:

an input vessel for receiving soil;

water delivery means for delivering water to the input vessel; and a mixer coupled relative to the vessel to mix the water and soil to form a slurry.

5. The apparatus of claim 4 wherein the sample input section further comprises:

a doser, coupled to the input vessel, for removing a slurry sample comprising at least a portion of the slurry from the input vessel; and dry content determining means, coupled to the doser, for receiving the slurry sample from the doser and determining a dry content of the slurry sample.

6. The apparatus of claim 5 wherein the dry content determining means comprises:

a humidity meter for measuring humidity of the slurry sample;

a scale for measuring a weight of the slurry sample; and wherein the controller is coupled to the humidity meter and the scale and wherein the controller determines a weight of the dry content of the slurry sample.

7. The apparatus of claim 5 wherein the sample input section further comprises:

a filter coupled between the doser and the dry content determining means for filtering the slurry sample before the slurry sample enters the dry content determining means.

8. The apparatus of claim 1 wherein the sample input section comprises:

an opener for receiving sealed packages containing soil and for opening the packages, the input vessel receiving the soil from the opener.

9. The apparatus of claim 1 wherein the testing stations comprise:

a first plurality of test stations, each for determining a nutrient of the soil samples; and a second plurality of test stations, each for determining a physical characteristic of the soil samples.

10. The apparatus of claim 1 further comprising:

washing means arranged relative to the continuous conveyor for washing the vessels after a last of the testing stations has accessed the sample contained in the vessel.

11. The apparatus of claim 2 wherein the controller determines nutrients to be applied to a field represented by the soil sample.

12. A method of analyzing a plurality of soil samples to determine characteristics of the soil samples, comprising:

receiving a first soil sample;

mixing the soil sample with a liquid to form a slurry;

providing the slurry to a vessel supported for movement with a continuous conveyor;

controlling the continuous conveyor to sequentially move the vessel to a plurality of test stations;

determining a characteristic at each test station; and repeating the steps of receiving, mixing, providing, controlling and determining for a subsequent soil sample so that a plurality of soil samples are at test stations simultaneously.

13. The method of claim 12 and further comprising, after the step of mixing, determining a dry content of the slurry.

14. The method of claim 13 wherein determining a dry content of the slurry comprises:

determining a humidity of the slurry a plurality of times to obtain a plurality of humidity values;

obtaining a final humidity value based on the plurality of humidity values; and using the final humidity value in obtaining the dry content of the slurry.

15. The method of claim 14 wherein the humidity is determined by taking measurements with a humidity meter and wherein the method comprises:

rinsing the humidity meter between measurements of slurries formed with different soil samples.

16. The method of claim 12 wherein determining a characteristic comprises:

agitating the slurry;

measuring sedimentation in the slurry by measuring light transmission characteristics of the slurry; and determining particle size of particles in the slurry based on the light transmission characteristics.

17. An apparatus for analyzing a plurality of soil samples to determine characteristics of the soil samples, the apparatus comprising:

a sample input section providing a plurality of soil samples each having a known solid content;

a conveyor;

a plurality of vessels supported for movement with the conveyor relative to the sample input section to receive the soil samples;

a plurality of accessing members arranged relative to the conveyor to sequentially access the samples carried by the vessels, the accessing members each accessing the samples so the samples can be tested to determine at least one of the characteristics of the samples; and wherein the plurality of vessels and the plurality of accessing members are movable relative to one another so that the plurality of vessels are advancable with the conveyor without interfering with the plurality of accessing members.

18. The apparatus of claim 17 further comprising:

a movable support member coupled to the plurality of accessing members moving the plurality of accessing members out of interference with the plurality of vessels so the plurality of vessels can be advanced by the conveyor.

19. The apparatus of claim 17 further comprising:

a second set of accessing members arranged relative to the conveyor and to the plurality of accessing members so that any of the plurality of accessing members are replaceable by corresponding ones of the second set of accessing members to sequentially access the samples carried by the vessels when any of the plurality of accessing members malfunctions.

20. An apparatus for analyzing a plurality of soil samples to determine characteristics of the soil samples, the apparatus comprising:

a sample input section sequentially providing a plurality of soil samples each having a known solid content;

a conveyor;

a plurality of vessels supported for movement with the conveyor relative to the sample input section to receive the soil samples; and a plurality of testing stations arranged relative to the conveyor to sequentially access the samples carried by the vessels, the testing stations each testing the samples to determine at least one of the characteristics of the samples, the testing stations comprising:

a carbon content analyzer including an acid introducer introducing an acid into a vessel containing the soil sample, a gas collector collecting gas produced by the acid and soil sample; volume determining means for determining a volume of the gas produced; and means for determining carbon content based on the volume of gas produced.

21. The apparatus of claim 20 wherein the gas collector comprises:

a container coupled to the vessel containing the soil sample and the acid and being filled to a reference level with liquid;

a reservoir providing the liquid to the container such that when gas enters the container from the vessel, the gas forces at least a portion of the liquid back into the reservoir; and wherein the volume determining means determines the volume of the gas collected based on an amount the fluid has dropped from the reference level.

22. The apparatus of claim 21 wherein the volume determining means comprises:

a pump for pumping liquid back into the container to the reference level; and means for determining a volume of the liquid pumped back into the container to return the liquid to the reference level to obtain the volume of gas collected.

23. The apparatus of claim 22 wherein the acid comprises hydrochloric acid and wherein the gas comprises carbonic acid gas.

24. The apparatus of claim 22 wherein the volume determining means comprises:

a liquid sensitive electrode arranged relative to the container to provide a signal indicating when the liquid is at the reference level.

25. An apparatus for analyzing a plurality of soil samples to determine characteristics of the soil samples, the apparatus comprising:

a sample input section sequentially providing a plurality of soil samples each being mixed into a soil slurry having a known solid content;

a conveyor;

a plurality of vessels supported for movement with the conveyor relative to the sample input section to receive the soil samples;

a plurality of testing stations arranged relative to the conveyor to sequentially access the samples carried by the vessels, the testing stations each testing the samples to determine at least one of the characteristics of the samples, the testing stations comprising:

a nutrient analyzer including at least one ion-selective electrode, and means for removing a portion of an extraction from the slurry in a vessel and generating an extraction flow, the ion-selective electrode being positioned in the flow and generating a signal indicative of a nutrient in the flow.

26. The apparatus of claim 25 wherein the nutrient analyzer comprises:

a plurality of ion-selective electrodes positioned in the flow to provide a plurality of signals indicative of a plurality of nutrients in the flow.

27. The apparatus of claim 25 wherein the means for removing a portion of the extraction from the slurry comprises:

a selectively pressurized conduit coupled to the vessel; and a ceramic filter filtering the slurry removed from the vessel.

28. The apparatus of claim 27 and further comprising:

means for providing a back pressure across the ceramic filter to clean the filter between soil samples.

29. The apparatus of claim 25 wherein the ion-selective electrode provides a signal indicative of at least one of the group consisting of NO3, NH4, K, P, Ca, Mg.

30. The apparatus of claim 26 and further comprising means for determining the nutrients based on interference effects of the nutrients indicated by the signals provided by the plurality of ion-selective electrodes.

31. The apparatus of claim 25 and further comprising:

means for evaporating a portion of the extraction; and means for increasing ion concentration in the extraction by adding a buffer.

32. The apparatus of claim 31 wherein the buffer comprises:

an MES buffer having a pH of approximately 6.15.

\* \* \* \* \*